US007163529B2

(12) United States Patent  (10) Patent No.: US 7,163,529 B2
Mocadlo  (45) Date of Patent: Jan. 16, 2007

(54) ABSORBENT ARTICLE HAVING DISPOSAL WINGS WITH ODOR ABSORBENCY

(75) Inventor: Cheryl Ann Mocadlo, New London, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/013,047

(22) Filed: Dec. 15, 2004

(65) Prior Publication Data
US 2006/0129118 A1 Jun. 15, 2006

(51) Int. Cl.
A61F 13/47 (2006.01)
A61F 13/476 (2006.01)

(52) U.S. Cl. .................... 604/385.04; 604/359
(58) Field of Classification Search ........... 604/385.04, 604/359, 360, 385.03
See application file for complete search history.

(56) References Cited

U.S. PATENT DOCUMENTS

| | | | |
|---|---|---|---|
| 3,707,148 A * | 12/1972 | Bryce | 604/360 |
| 4,186,743 A | 2/1980 | Steiger | |
| 4,589,876 A | 5/1986 | Van Tilburg | |
| 4,608,047 A * | 8/1986 | Mattingly | 604/387 |
| 4,687,478 A | 8/1987 | Van Tillburg | |
| 4,762,738 A | 8/1988 | Keyes et al. | |
| 4,846,828 A | 7/1989 | Mendelsohn | |
| 4,900,320 A | 2/1990 | McCoy | |
| 4,917,675 A * | 4/1990 | Taylor et al. | 604/385.02 |
| 4,930,942 A | 6/1990 | Keyes et al. | |
| 4,940,157 A | 7/1990 | Inagaki | |
| 4,963,140 A | 10/1990 | Robertson et al. | |
| 5,085,338 A | 2/1992 | Inagaki | |

(Continued)

FOREIGN PATENT DOCUMENTS

DE 42 26 739 A1 2/1994

(Continued)

OTHER PUBLICATIONS

INDA Standard Test Method IST 70.4 (99), "Standard Test Method for Water Vapor Transmission Rate Through Non Woven and Plastic Film Using a Guard Film and Vapor Pressure Sensor," Copyright 1995, 7 pages.

(Continued)

Primary Examiner—Tatyana Zalukaeva
Assistant Examiner—Paula L. Craig
(74) Attorney, Agent, or Firm—Paul Yee

(57) ABSTRACT

An absorbent article (20) has a longitudinal-direction (22), a lateral cross-direction (24), an overall longitudinal article-length, an overall lateral article-width, and an intermediate portion (76) interposed between a pair of longitudinally opposed end portions (72). The article comprises a backsheet (28), a liquid-permeable topsheet (26), an absorbent body (30) sandwiched between the backsheet (28) and the topsheet (26) and at least one wing-panel (42) which is operatively connected to the intermediate portion (76) of the article (20). The wing-panel extends laterally beyond at least one lateral side edge of the backsheet (28) in the intermediate portion (76) of the article, and the wing-panel (42) is configured to wrap about an undergarment. The wing-panel includes an operative quantity of odor-control material, and at least one, laterally-outboard wing-section of the wing-panel (42) can be sufficiently sized and shaped to operatively enclose the article (20) for disposal.

18 Claims, 9 Drawing Sheets

U.S. PATENT DOCUMENTS

| | | | |
|---|---|---|---|
| 5,267,992 A | 12/1993 | Van Tilburg | |
| 5,268,105 A | 12/1993 | Uejima et al. | |
| 5,279,604 A | 1/1994 | Robertson et al. | |
| 5,476,456 A | 12/1995 | Rankin et al. | |
| 5,478,336 A * | 12/1995 | Pigneul | 604/385.04 |
| 5,532,350 A | 7/1996 | Cottrell et al. | |
| 5,584,954 A | 12/1996 | Van Der Klugt | |
| 5,591,146 A | 1/1997 | Hasse | |
| 5,591,147 A | 1/1997 | Couture-Dorschner et al. | |
| 5,660,665 A | 8/1997 | Jalonen | |
| 5,669,898 A * | 9/1997 | Ahr | 604/387 |
| H1732 H * | 6/1998 | Johnson | 428/68 |
| 5,762,645 A | 6/1998 | Peck et al. | |
| 5,769,832 A | 6/1998 | Hasse | |
| 5,769,833 A * | 6/1998 | Hasse | 604/359 |
| 5,772,650 A * | 6/1998 | Mizutani | 604/387 |
| 5,858,515 A | 1/1999 | Stokes et al. | |
| 5,951,534 A * | 9/1999 | Cummings et al. | 604/359 |
| 5,985,396 A | 11/1999 | Kerins et al. | |
| 5,993,430 A * | 11/1999 | Gossens et al. | 604/385.02 |
| 6,093,178 A | 7/2000 | Osborn, III et al. | |
| 6,203,512 B1 | 3/2001 | Farris et al. | |
| 6,277,105 B1 * | 8/2001 | Rynish | 604/385.02 |
| 6,284,261 B1 * | 9/2001 | Tramontana | 424/430 |
| 6,403,113 B1 | 6/2002 | Corzani | |
| 6,432,098 B1 | 8/2002 | Kline et al. | |
| 6,437,211 B1 | 8/2002 | Kaye et al. | |
| 6,468,517 B1 | 10/2002 | Moscherosch | |
| 6,544,242 B1 | 4/2003 | Kido et al. | |
| 6,630,233 B1 | 10/2003 | Levandowski et al. | |
| 6,632,494 B1 | 10/2003 | Okubo et al. | |
| 6,702,116 B1 | 3/2004 | Hummel | |
| 2002/0013566 A1 | 1/2002 | Chappell et al. | |
| 2002/0018761 A1 | 2/2002 | Moscherosch | |
| 2002/0058921 A1 | 5/2002 | Sigl | |
| 2002/0068917 A1 | 6/2002 | VanGompel et al. | |
| 2002/0078665 A1 | 6/2002 | Salman et al. | |
| 2002/0110689 A1 * | 8/2002 | Hu et al. | 428/375 |
| 2002/0143311 A1 * | 10/2002 | Brisebois | 604/385.01 |
| 2002/0169431 A1 | 11/2002 | Kline et al. | |
| 2002/0170275 A1 | 11/2002 | Salman et al. | |
| 2003/0004484 A1 | 1/2003 | Hammons et al. | |
| 2003/0036740 A1 | 2/2003 | Hammonds et al. | |
| 2003/0105183 A1 * | 6/2003 | Sharak | 523/102 |
| 2003/0114806 A1 | 6/2003 | La Fortune | |
| 2003/0114812 A1 | 6/2003 | Braverman et al. | |
| 2003/0127343 A1 | 7/2003 | Hummel | |
| 2003/0153891 A1 | 8/2003 | Molee | |
| 2004/0030315 A1 | 2/2004 | Brooks | |
| 2004/0067214 A1 | 4/2004 | Krautkramer et al. | |
| 2004/0083887 A1 | 5/2004 | Simpson et al. | |
| 2004/0116882 A1 * | 6/2004 | Erspamer et al. | 604/359 |
| 2004/0121681 A1 | 6/2004 | Lindsay et al. | |
| 2004/0122387 A1 | 6/2004 | Long et al. | |
| 2004/0186448 A1 | 9/2004 | Misek et al. | |
| 2005/0113771 A1 | 5/2005 | MacDonald et al. | |
| 2005/0124959 A1 * | 6/2005 | Alcantara et al. | 604/385.04 |
| 2005/0131372 A1 * | 6/2005 | Wheeler et al. | 604/385.04 |
| 2005/0183814 A1 | 8/2005 | Alcantara et al. | |
| 2005/0187531 A1 * | 8/2005 | Alcantara et al. | 604/385.04 |
| 2006/0030828 A1 * | 2/2006 | Wilhelm et al. | 604/359 |

FOREIGN PATENT DOCUMENTS

| | | | |
|---|---|---|---|
| EP | 1 062 928 A1 | | 12/2000 |
| EP | 1245209 | * | 10/2002 |
| WO | WO 93/06805 A1 | | 4/1993 |
| WO | WO 94/27542 A1 | | 12/1994 |
| WO | WO 99/65439 A1 | | 12/1999 |
| WO | WO 99/65440 A1 | | 12/1999 |
| WO | WO 01/00122 A1 | | 1/2001 |
| WO | WO 2002/083047 | | 10/2002 |

OTHER PUBLICATIONS

Patent Cooperation Treaty Search Report from the International Search Authority, International Application No. PCT/US 2005/033124 dated Jan. 23, 2006.

* cited by examiner

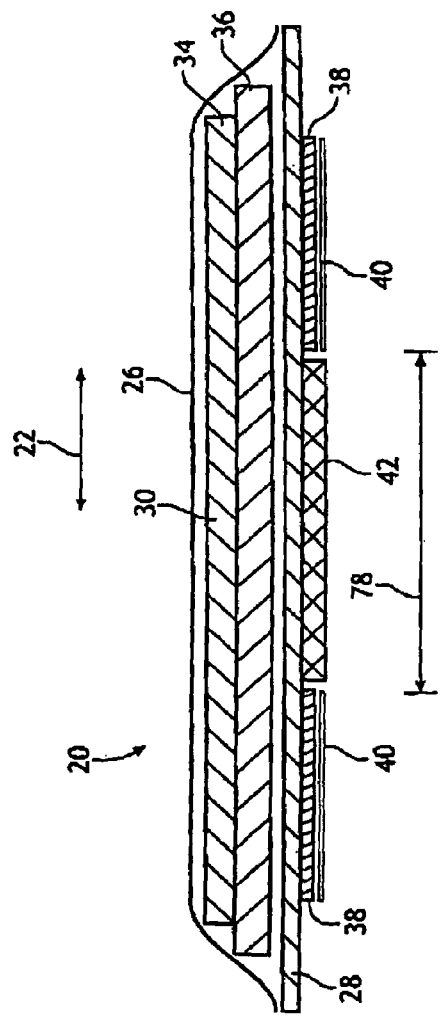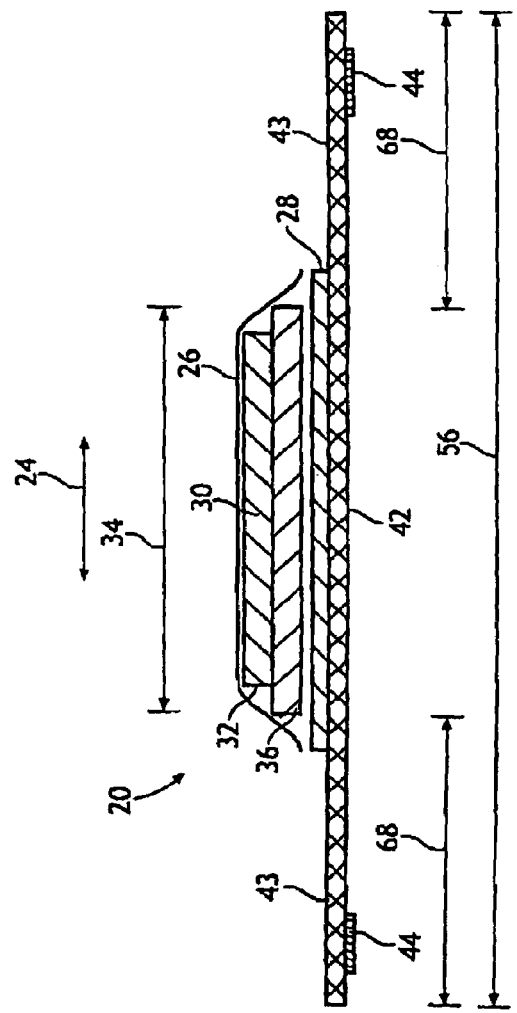
FIG. 2
FIG. 2A

US 7,163,529 B2

ABSORBENT ARTICLE HAVING DISPOSAL WINGS WITH ODOR ABSORBENCY

FIELD OF THE INVENTION

The present invention relates to a fastening system for an absorbent article. More particularly, the present invention pertains to a feminine care article, such as a feminine care pad, having a system of one or more wing-panels.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that, feminine care articles have been employed to absorb and hold liquids, such as urine and/or menses. In particular arrangements, the feminine care articles have included wing portions which can help to hold the article in place at a selected location in a wearer's undergarment. In some arrangements, the wing portions have been integrally formed with one or more of the preexisting component layers that were employed to construct the article. In other arrangements, the wing portions have been separately provided components that are assembled and affixed to the final product. Various fasteners have been employed to secure the wing portions in a desired configuration during ordinary use. The fasteners have included adhesive fasteners as well as mechanical fasteners, and the mechanical fasteners have included conventional, hook-and-loop fasteners.

Conventional absorbent articles have also included wrappers, pouches and other packaging. The packaging has been employed to hold a soiled article for disposal. Additionally, soiled articles have been folded and wing portions of the articles have been employed to hold the soiled articles in the folded condition for disposal.

Conventional absorbent articles with wing portions, however, have not provided desired combinations of securement, comfort, performance and versatility. When conventional articles have been constructed with integrally formed wing components, it has been difficult to provide the wing portions with desired, differentiated characteristics, such as odor-control characteristics. When conventional articles have been constructed with separately provided wing components, the finished product has not provided sufficient levels of aesthetic appeal and attractiveness. In addition, there has been a continued need for an improved article design that provides a more effective and convenient system for placing a soiled article in a condition that provides operative odor-control while also holding the soiled article in a desired disposal condition.

BRIEF DESCRIPTION OF THE INVENTION

Generally stated, the present invention provides an absorbent article having a longitudinal direction, a lateral direction, first and second longitudinally opposed end portions, and an intermediate portion located between the end portions. The article comprises an absorbent body sandwiched between a backsheet and a liquid-permeable topsheet. At least one wing-panel which is operatively connected to the intermediate portion of the article. The wing-panel extends laterally beyond at least one lateral side edge of the backsheet in the intermediate portion of the article, and the wing-panel is configured to wrap about an undergarment. In a particular feature, the wing-panel can include an operative quantity of odor-control material. In another feature, at least one, laterally-outboard wing-section of the wing-panel can be sufficiently sized and shaped to operatively enclose the article for disposal. In a further feature, the wing-panel can be configured to operatively provide a wing-section distance which is at least about 50% of a width of the absorbent body By incorporating its various features and configurations, the article of the invention can provide the versatility and enhanced performance that can arise from incorporating separately provided wing portions that are constructed from different materials having selected characteristics and performance parameters. Additionally, the article of the invention can provide a more effective and convenient system for placing a soiled article in a condition that provides operative odor-control while also holding the soiled article in a desired disposal condition.

BRIEF DESCRIPTION OF THE DRAWINGS

The various features, aspects and advantages of the present invention will become better understood with reference to the following description, appended claims and accompanying drawings where:

FIG. 2 shows a partially-expanded schematic view of a representative, longitudinal cross-section of a representative feminine care article.

FIG. 2A shows a partially-expanded schematic view of a representative, transverse cross-section of a representative feminine care article.

DETAILED DESCRIPTION OF THE INVENTION

Figure 1:
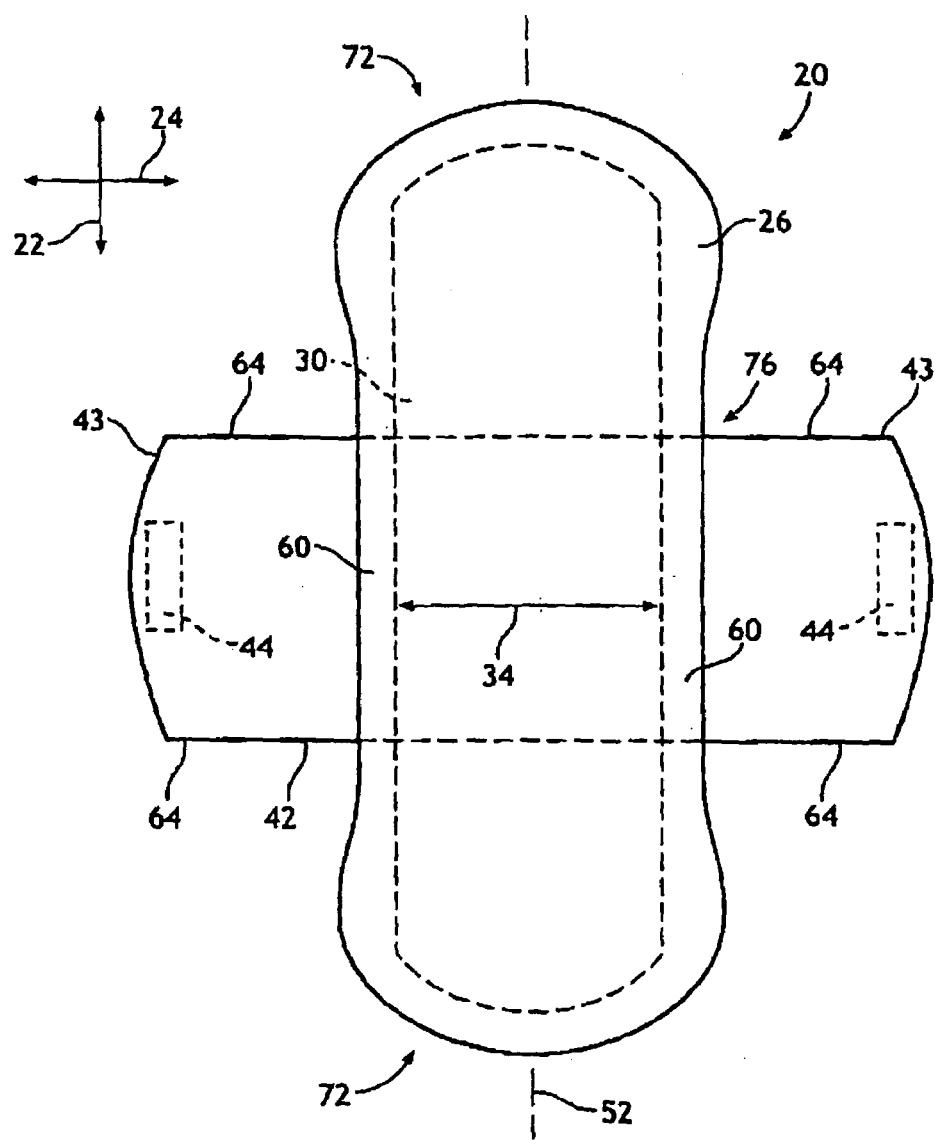
FIG. 1 shows a top, plan view of a bodyside of a representative feminine care article having a singular wing-panel positioned adjacent an outside surface of the article, in which side portions of the wing-panel are arranged in a laterally-extended position.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an absorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, a substantially liquid impervious backsheet operatively connected to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof, can operate to provide a body-facing surface and a garment-facing surface. As used herein, "body-facing surface" means that surface of the article or component which is intended to be disposed toward or placed adjacent to the body of the wearer during ordinary use, while the "outward surface" or "outward-facing surface" is on the opposite side, and is intended to be disposed to face away from the wearer's body during ordinary use. The outward surface may be arranged to face toward or placed adjacent to the wearer's undergarments when the absorbent article is worn.

FIGS. 1 through 4 illustrate examples of a suitable article 20, such as the representatively shown feminine care article, which is configured to incorporate the present invention. The feminine care article can, for example, be a feminine care pad or napkin, and the article can have a lengthwise longitudinal direction 22, a transverse, laterally extending, cross-direction 24, first and second longitudinally opposed end portions 72, and an intermediate portion 76 located between the end portions. As representatively shown, the longitudinal dimension of the article is relatively larger than the lateral dimension of the article. The article 20 can include a baffle or backsheet 28, a liquid-permeable cover or topsheet 26, and an absorbent body structure 30 which is operatively positioned and sandwiched between the backsheet 28 and topsheet 26. As representatively shown, peripheries of the topsheet and backsheet may be substantially entirely coterminous. Alternatively, the peripheries of the topsheet 26 and the backsheet 28 may be partially or entirely non-coterminous. At least one wing-panel member 42 can be operatively connected to the intermediate portion 76 of the article 20. In particular aspects of the article, the wing-panel can extend laterally beyond at least one lateral side edge of either or both of the topsheet 26 and backsheet 28 in the article intermediate portion 76, and the wing-panel 42 can be configured to wrap about an undergarment, particularly a crotch section of the undergarment.

In a desired feature, a maximum longitudinal length 58 of the wing panel 42 can be less than a maximum longitudinal length 48 of the backsheet 28. Another feature can include a singular wing-panel that is positioned and configured to extend transversely beyond a laterally opposed pair of side edges of the absorbent body 30, topsheet 26 and/or backsheet 28. Optionally, a cooperating plurality of wing-panels 42 can be operatively connected to the article intermediate portion 76, and each of the wing-panels can be configured to extend transversely beyond a corresponding side edge of the backsheet 28. In particular aspects, the wing-panel can include an operative quantity of odor-control material, and an overall arrangement of one or more laterally-outboard wing-sections 43 of the wing-panel 42 can be sufficiently sized and shaped to operatively enclose the article 20 for disposal. In other aspects, the wing-panel can be configured to operatively provide a wing-section distance 68 which is at least about 50% of a width of the absorbent body.

By incorporating its various aspects, features and configurations (alone or in desired combinations), the article of the invention can provide the versatility and enhanced performance that can arise from incorporating separately provided wing portions that are constructed from different materials having selected characteristics and performance parameters, such as improved odor-control. Additionally, the article of the invention can provide a more effective and convenient system for placing a soiled article in a condition that provides operative odor-control while also holding the soiled article in a desired disposal condition.

The cover or topsheet 26 may include any material that can be configured to provide the topsheet with an operative level of liquid-permeability. The topsheet may be constructed with one or more layers of suitable materials, and may be a composite material. For example, the topsheet layer can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded-web, a bicomponent spunbond fabric or the like as well as combinations thereof. For example, the topsheet layer can include a woven fabric, a nonwoven fabric, a polymeric film that has been configured to be operatively liquid-permeable, or the like, as well as combinations thereof. Other examples of suitable materials for constructing the topsheet layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A more particular example of a suitable topsheet layer material can include a bonded-carded-web composed of polypropylene and polyethylene, such as has been used as a topsheet stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the topsheet layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the topsheet layer. The apertures or other openings can help increase the rate at which bodily liquids can move through the thickness of the topsheet layer and penetrate into the other components of the article (e.g. into the absorbent structure 30). The selected arrangement of liquid-permeability is desirably present at least on an operative portion of the topsheet layer that is appointed for placement on the body-side of the article. The topsheet layer 26 can provide comfort and conformability, and can function to direct bodily exudates away from the body and toward the absorbent structure 30. In a desired feature, the topsheet layer 26 can be configured to retain little or no liquid in its structure, and can be configured to provide a relatively comfortable and non-irritating surface next to the body-tissues of a female wearer. The topsheet layer 26 can be constructed of any material which is also easily penetrated by bodily fluids that contact the surface of the topsheet layer.

The topsheet 26 can also have at least a portion of its bodyside surface treated with a surfactant to render the topsheet more hydrophilic. The surfactant can permit arriving bodily liquids to more readily penetrate the topsheet layer. The surfactant may also diminish the likelihood that the arriving bodily fluids, such as menstrual fluid, will flow off the topsheet layer rather than penetrate through the topsheet layer into other components of the article (e.g. into the absorbent body structure). In a particular configuration, the surfactant can be substantially evenly distributed across at least a portion of the upper, bodyside surface of the topsheet 26 that overlays the upper, bodyside surface of the absorbent.

The topsheet 26 may be maintained in secured relation with the absorbent structure 30 by bonding all or a portion of the adjacent surfaces to one another. A variety of bonding techniques known to one of skill in the art may be utilized to achieve any such secured relation. Examples of such techniques include, but are not limited to, the application of adhesives in a variety of patterns between the two adjoining surfaces, entangling at least portions of the adjacent surface of the absorbent with portions of the adjacent surface of the topsheet, or fusing at least portions of the adjacent surface of the topsheet to portions of the adjacent surface of the absorbent.

The topsheet 26 typically extends over the upper, bodyside surface of the absorbent structure to provide a bodyside liner, but can alternatively extend around the article to partially or entirely, surround or enclose the absorbent structure. Alternatively, the topsheet 26 and the backsheet 28 can have peripheral margins which extend outwardly beyond the terminal, peripheral edges of the absorbent structure 30, and the extending margins can be connected together to partially or entirely, surround or enclose the absorbent structure.

The baffle or backsheet 28 may include a layer constructed of any operative material, and may or may not be configured to be liquid-permeable. In a particular configuration, the cover or backsheet 28 may be configured to provide an operatively liquid-impermeable layer. The backsheet may, for example, include a polymeric film, a woven fabric, a nonwoven fabric or the like, as well as combinations or composites thereof. For example, the backsheet may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the backsheet 28 can operatively permit a sufficient passage of air and moisture vapor out of the article, particularly out of an absorbent (e.g. storage or absorbent structure 30) while blocking the passage of bodily liquids. An example of a suitable backsheet material can include a breathable, microporous film, such as a HANJIN Breathable backsheet available from Hanjin Printing, Hanjin P&C Company Limited, a business having offices located in Sahvon-Ii.Jungan-mvu.Kongiu-City, Chung cheong nam-do, Republic of South Korea. The backsheet material is a breathable film, which is white in color, dimple embossed, and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed cell polyolefin foam. For example, a closed cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., USA.

The structure of the absorbent body 30 can be operatively configured to provide a desired level of absorbency or storage capacity. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural and/or synthetic fiber.

The absorbent structure 30 may also include superabsorbent material. Superabsorbent materials suitable for use in the present invention are known to those skilled in the art, and may be in any operative form, such as particulate form. Generally stated, the water-swellable, generally water-insoluble, hydrogel-forming polymeric absorbent material (superabsorbent) is capable of absorbing at least about 10, desirably about 20, and possibly about 100 times or more its weight in water. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company, Hoechst Celanese Corporation, Allied Colloid Inc., and Degussa Superabsorber Stockhausen, Inc.

The absorbent body 30 can be substantially unitary with a non-uniform structure or a generally uniform structure. Alternatively, the absorbent body may include a composite structure having a selected plurality of strata or layers. For example, the absorbent body structure may include an intake layer, a distribution layer, a transfer layer, a transfer-delay layer, a shaping layer, a retention layer or the like, as well as combinations thereof. The various strata and/or layers may be layered or otherwise arranged in any operative sequence or configuration. Examples of an absorbent article having a composite absorbent body are described in detail in U.S. Patent Application Publication 20040186448 entitled MULTILAYER ABSORBENT ARTICLE by Misek et al., which was published Sep. 23, 2004, the entire disclosure of which is incorporated herein by reference in a manner that is consistent herewith.

The absorbent body 30 can also have any operative shape. The absorbent body shape may be rectilinear, curvilinear, oval, race-track shaped, hourglass shaped, dog bone shaped or the like, as well as combinations thereof. Additionally, the absorbent article can include any desired pattern or array of embossments. In particular aspects, the embossments may be formed on the bodyside surface of the article. Desired arrangements can include an absorbent body structure that has embossment regions formed on at least its bodyside surface. Similarly, the other employed components of the article can also include corresponding embossed regions.

Figure 1A:
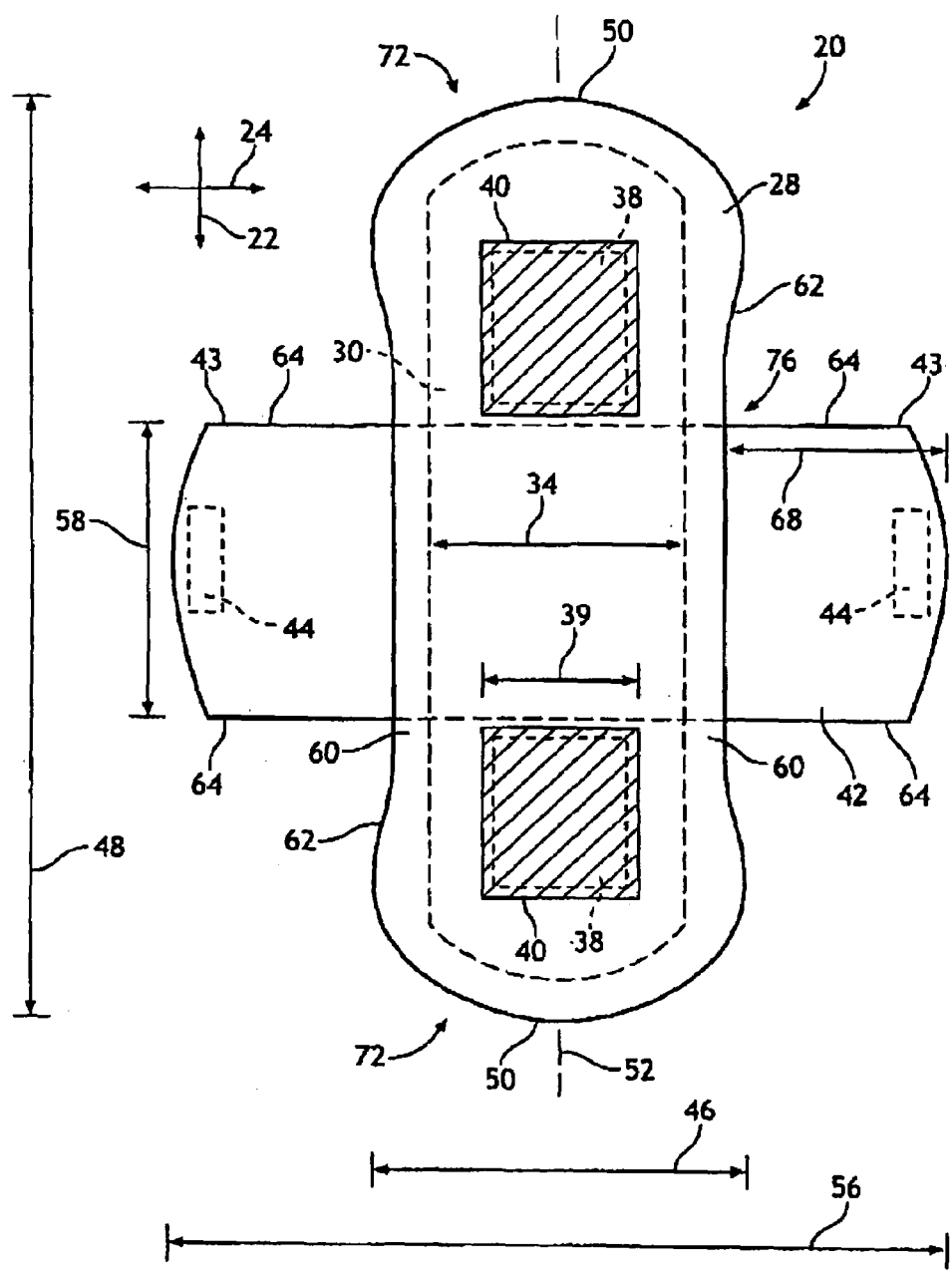
FIG. 1A shows a bottom, plan view of a garment-side of the representative feminine care article illustrated in FIG. 1.
Figure 3:
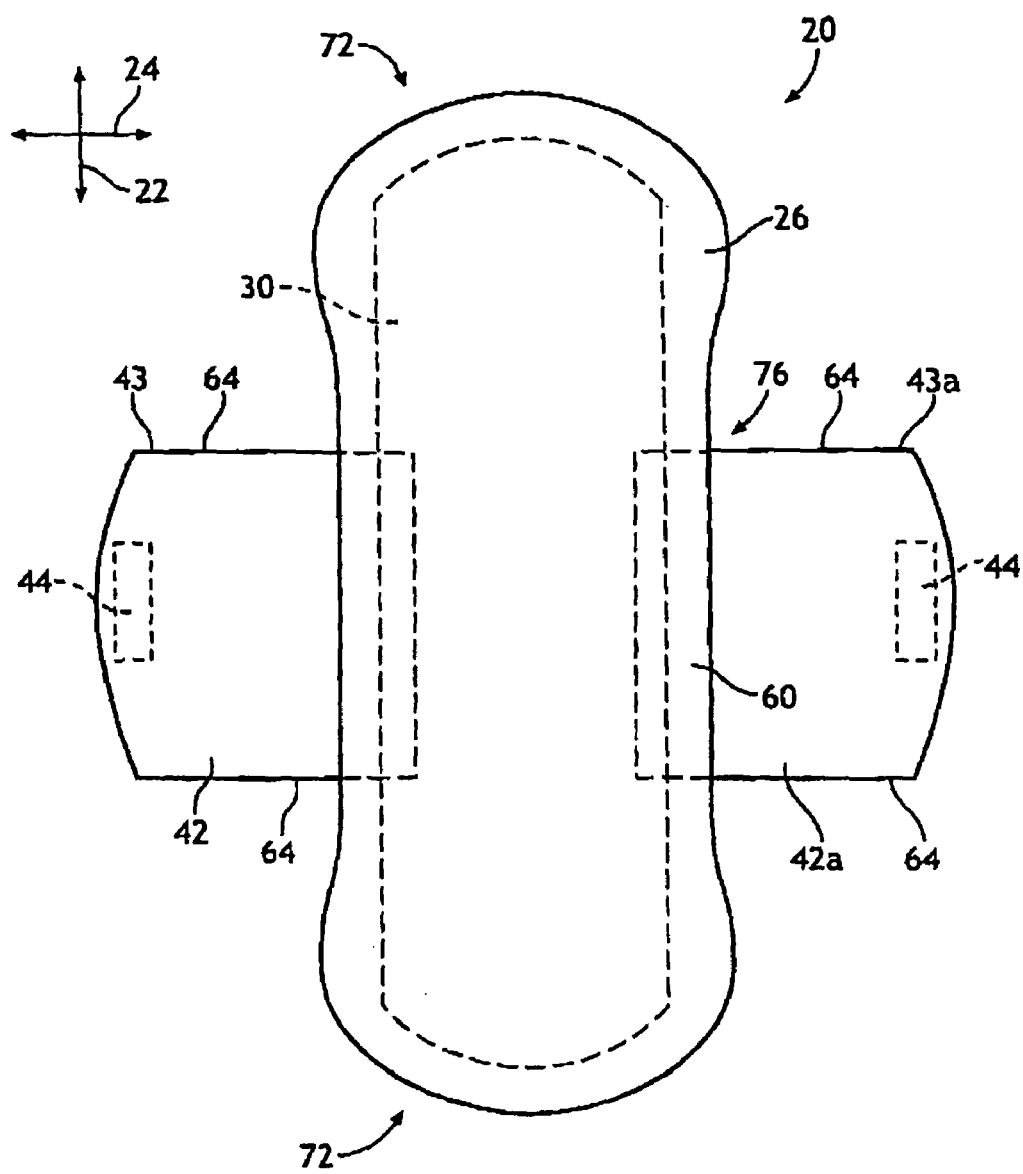
FIG. 3 representatively shows a top plan view of the bodyside of another representative feminine care article in which a plurality of separately provided wing-panel portions are arranged in a laterally-extended position and located adjacent an outside surface of the article.
Figure 3A:
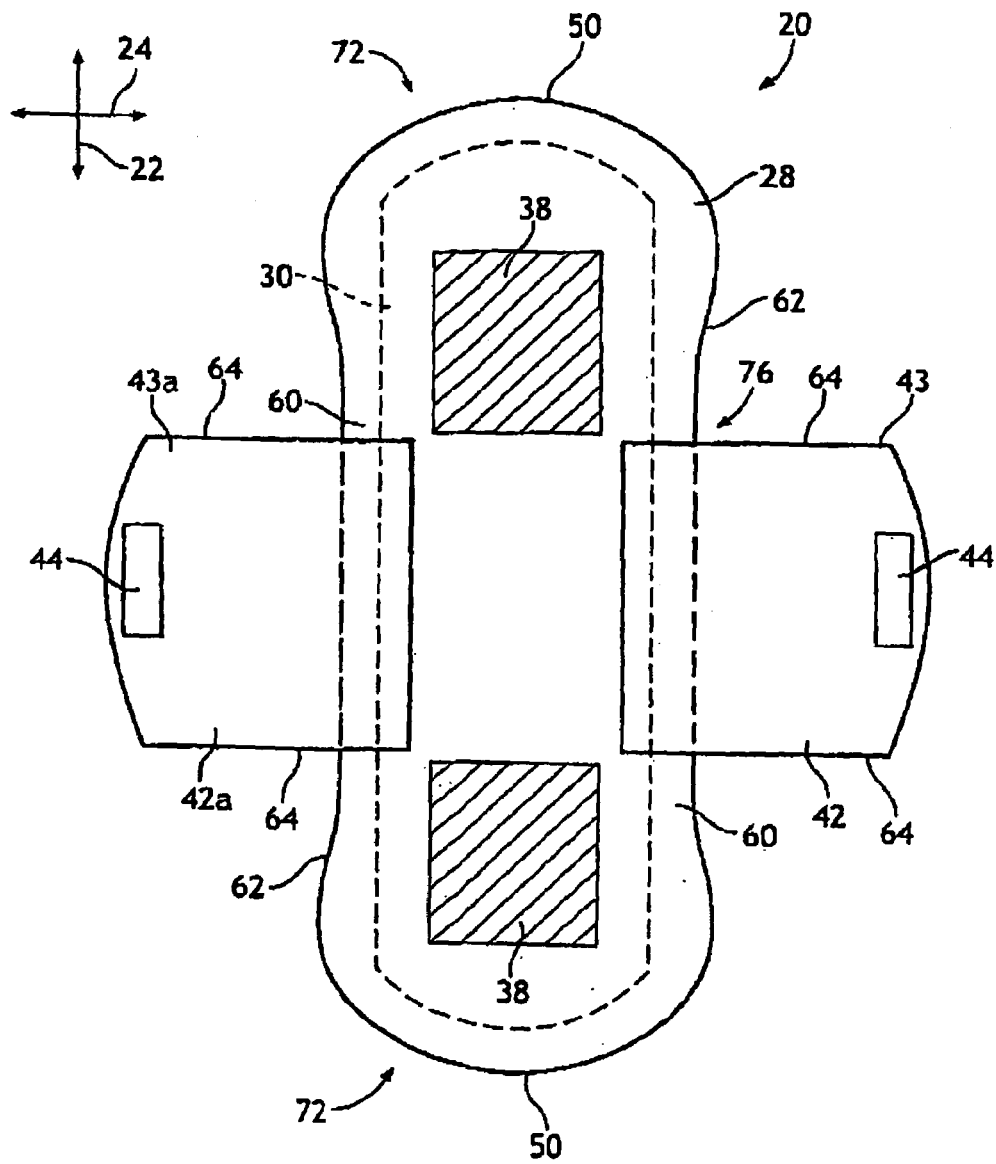
FIG. 3A shows a bottom, plan view of a garment-side of the representative feminine care article illustrated in FIG. 3.

With reference to FIGS. 1A, 2 and 3A, a selected configuration of a garment-fastener mechanism may be operatively distributed and connected onto the garment-side of the article 20 to help secure the article to the undergarment. The garment-fastener can include any operative fastener mechanism, such as a component of an interengaging mechanical fastener, an adhesive fastener, a cohesive fastener, a magnetic fastener, and electromechanical fastener or the like, as well as combinations thereof. For example, the garment-fastener be provided by the representatively shown adhesive 38, and the adhesive may be arranged in the illustrated strip regions that are distributed onto the garment-side of the article. Typically, the garment adhesive can be distributed over the garment-side of the backsheet, and one or more layers or sheets of release material 40 can be removably placed over the garment adhesive during storage prior to use.

To help hold the article in the desired disposal configuration and provide better odor control, the garment adhesive or other garment-fastener can be distributed in a pattern in which the laterally opposed side edge regions of the garment-fastener delimit a garment-fastener width 39. In a particular aspect, the garment-fastener width can be up to a maximum of about 100% of a width 34 of the absorbent body 30. The garment-fastener width can alternatively be up to about 90%, and optionally up to about 80% of the absorbent body width 34 to provide desired performance. In another aspect, the garment-fastener width 39 can be at least a minimum of about 30% of the absorbent body width. The garment-fastener width can alternatively be at least about 50%, and optionally at least about 60% of the absorbent body width 34 to provide improved performance.

To help provide improved disposal, the garment adhesive or other garment-fastener can be distributed in a pattern in which the garment-side surface of the wing-panel is substantially free of the garment-fastener. In particular aspects, the garment-side surface of the wing-panel can be substantially free of a garment adhesive. In other aspects, the garment-fastener can be substantially absent from the garment-side surface of the wing-panel along a selected zone of the article intermediate portion 76. Desired configurations of the article can have the garment-fastener configured to be substantially absent from the article intermediate section 76 along a longitudinally extending, zone distance length 78 (e.g. FIG. 2). The zone distance with desired values can help prevent unwanted attachment to other household surfaces such as waste containers when the article is arranged in its disposal condition.

In a particular aspect, the zone distance 78 can be at least a minimum of about 15% of the backsheet length 48. The zone distance can alternatively be at least about 25% of the backsheet length, and can optionally be at least about 30% of the backsheet length to provide desired performance. In another aspect, the zone distance can be up to a maximum of about 85% of the backsheet length 48, or more. In other arrangements, the zone distance can be up to about 60% of the backsheet length. The zone distance can alternatively be up to about 45% and optionally be up to about 40% of the backsheet length. In a particular arrangement, the zone distance can extend at least about one-third of the backsheet length.

In desired arrangements, the zone distance 78 can be up to about 14 cm. The zone distance can alternatively be up to about 10.5 cm, and can optionally be up to about 9.5 cm. In further arrangements, the zone distance 78 can be at least about 3.5 cm. The zone distance can alternatively be at least about 6 cm, and can optionally be at least about 7 cm to provide desired benefits.

As representatively shown, the article 20 can include a system of one or more wing-panel portions 42 positioned to extend along either or both lateral sides of the article. The wing-panels may be integrally formed from another component of the article, such as the topsheet and/or the backsheet, and operatively connected to appointed sections of the article side regions 60 along the intermediate portion 76 of the article. Desirably, the wing-panels or wings can be separately provided members that are subsequently attached or otherwise connected to the intermediate portion of the article 20.

The wing-panels can have an appointed storage position in which the wing-panels 42 are directed generally inwardly toward the longitudinally-extending centerline 52. The wing-panel that is connected to extend from one side margin may have sufficient cross-directional length to extend and continue past the centerline 52 to approach the laterally opposite side margin of the article. The storage position of the wing-panels can ordinarily represent an arrangement observed when the article is first removed from its wrapper or other packaging. Prior to placing the article into a bodyside of an undergarment prior to use, the wing-panels 42 can be selectively arranged to extend laterally from the side regions 60 of the article intermediate portion. After placing the article in the undergarment, the wing-panels 42 can be operatively wrapped and secured around the side edges of the undergarment crotch portion to help hold the article in place, in a well known, conventional manner.

The wing-panel portions 42 can have any operative construction, and can include a layer of any operative material. Additionally, each wing-panel can comprise a laminate or other composite material. For example, the wing-panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

The wing-panel materials can be substantially non-stretchable or otherwise non-extensible. Alternatively, the wing-panel may be stretchable or otherwise extensible to enlarged dimensions. In particular arrangements, the wing-panel material may also be capable of providing a selected amount of elastomeric stretch and retraction. For example, see U.S. Patent Application Publication No. 20040122387 entitled ABSORBENT ARTICLES THAT INCLUDE A STRETCHABLE SUBSTRATE HAVING ODOR CONTROL PROPERTIES by A. Long et al., which was published Jun. 24, 2004. In particular configurations, the wing-panel material can exhibit a maximum stretch elongation value of up to about 300%, or more. In other aspects, the wing-panel material can exhibit a minimum stretch elongation value of at least about 25% or at least about 50%. In further features, the wing-panel material can have a basis weight which is within the range of about 0.5–3 ounces per square yard (about 17–102 $g/m^2$). By employing such wing-panel materials, the wing-panel can provide better fit characteristics, and can help provide improved leak protection.

With reference to FIGS. 1, 1A and 2A, the wing-panel 42 can have a transverse-length 56 and a longitudinal-length 58. In desired configurations, a maximum longitudinal-length 58 of the wing panel 42 is less than a maximum longitudinal length of the article 20. For example, the maximum longitudinal length of the wing-panel 42 can be up to about 85% or more of a maximum longitudinal length 48 of the backsheet 28, but should be less than the longitudinal length of the backsheet. In a particular feature, the overall longitudinal-length of the wing-panel 42 can be up to about 60% of an overall longitudinal-length 48 of the backsheet 28. The overall longitudinal-length 58 of the wing-panel 42 can alternatively be up to about 45% of the overall longitudinal-length of the backsheet, and can optionally be up to about 40% of the overall longitudinal-length 48 of the backsheet 28 to provide improved benefits. In another feature, the overall longitudinal-length 58 of the wing-panel 42 can be not less than a minimum of about 15% of an overall longitudinal-length 48 of the backsheet 28. The longitudinal-length of the wing-panel can alternatively be not less than about 25% of the longitudinal-length of the backsheet, and can optionally be not less than about 30% of the longitudinal-length of the backsheet to provide improved performance. Additionally, the longitudinally opposed end-edges 64 of the wing-panel 42 are non-coterminous with the longitudinal end-edges 50 of the backsheet 28.

In desired arrangements the overall longitudinal-length 58 of the wing-panel 42 can be up to about 14 cm. The longitudinal-length of the wing-panel can alternatively be up to about 10.5 cm and can optionally be up to about 9.5 cm. In further arrangements, the longitudinal-length of the wing-panel 42 can be at least about 3.5 cm. The longitudinal-length of the wing-panel can alternatively be at least about 6 cm and can optionally be at least about 7 cm to provide desired benefits.

As representatively shown, at least one distal, outboard wing-section 43 of the wing-panel 42 can extend or can otherwise be configured to extend beyond each of the laterally-opposed side-edges of the absorbent body 30 along a laterally outboard, wing-section distance 68. Where the wing-panel 42 is a singular wing-panel, the wing-panel can extend or can otherwise be configured to extend beyond both of the laterally-opposed side-edges 62 of the backsheet 28 over the selected wing-section distance 68. As representatively shown, a transversely-opposed pair of cooperating wing-sections 43 can be configured to extend laterally outboard from the transversely-opposed side edges of the absorbent body 30 for the selected wing-section distance 68. The transversely-opposed pair of cooperating wing-sections can also be substantially aligned along the cross-direction 24, and can be substantially mirror-images of each other. In particular aspects, where the wing-panel 42 is provided by a substantially non-stretchable or otherwise substantially non-extensible material, the wing-section distance 68 can initially be configured to be at least a minimum of about 50% of an overall width 34 of the absorbent body 30. The wing-section distance can alternatively be at least about 60%, and can optionally be at least about 65% of the absorbent body width 34. In other aspects, the substantially non-extensible wing-section distance 68 can initially be up to a maximum of about 100% of the absorbent body width. The wing-section distance 68 can alternatively be up to about 90%, and can optionally be up to about 85% or 75% of the absorbent body width 34 to provide desired performance. In further aspects, the substantially non-extensible wing-section distance can initially be at least a minimum of about 3 centimeters (cm). The wing-section distance 68 can alternatively be at least about 3.5 cm, and can optionally be at least about 4 cm to provide improved performance. In other aspects, the substantially non-extensible wing-section distance 68 can initially be up to a maximum of about 10 cm, or more. The wing-section distance can alternatively be up to about 6 cm, and can optionally be up to about 5 cm to provide desired effectiveness.

Where the wing-panel 42 is provided by a stretchable or otherwise extensible material, the wing-panel can be operatively enlarged to the size and dimensions described with respect to the substantially non-extensible wing-panel. The extensible wing-section distance 68 can initially be at least a minimum of about 25% of an overall width 34 of the absorbent body 30. The wing-section distance can alternatively be at least about 33%, and can optionally be at least about 50% of the absorbent body width 34. In other aspects, the extensible wing-section distance 68 of the extensible wing-panel can initially be up to a maximum of about 100% of the absorbent body width. The wing-section distance 68 can alternatively be up to about 90%, and can optionally be up to about 85% or 75% of the absorbent body width 34 to provide desired performance. In further aspects, the extensible wing-section distance can initially be at least a minimum of about 1.5 centimeters (cm). The wing-section distance 68 can alternatively be at least about 2 cm, and can optionally be at least about 3 cm to provide improved performance. In other aspects, the extensible wing-section distance 68 can initially be up to a maximum of about 6 cm, or more. The wing-section distance can alternatively be up to about 5 cm, and can optionally be up to about 4 cm to provide desired effectiveness.

If the transverse-length and/or the longitudinal-length of the wing panel is outside the desired values, various problems can occur. Overly large wing-panels may, for example, fit poorly about a panty or other undergarment, and be inconvenient to apply and uncomfortable to wear. The overly large wing-panels can also cause excessive waste and poor processing. Overly small wing panels can also be insufficient to secure the soiled article in a desired disposal configuration, and may fit poorly around a panty or other undergarment. As a result, the article may be inconvenient to apply and uncomfortable to wear. For example, the wing panels may more readily detach and stick to the skin, causing discomfort.

The end-edge 64 of the wing-panel 42 may or may not provide a substantially continuous extension from the side-edge of the topsheet 26 and/or backsheet 28. Accordingly, as discerned by the ordinary, unaided human eye at a distance of 18 inch (46 cm) with no added magnification, there may or may not be a discrete angular break in the line of the article side-edge contour as one progresses from the side-edge 62 of the backsheet 28 onto the adjacent end-edge 64 of the wing panel 42. As representatively shown, the end-edge 64 of the wing-panel 42 can form and provide a substantially non-continuous extension from the side-edge 62 of the backsheet 28, and can also form and provide a substantially non-continuous extension from a corresponding, contoured side-edge of the topsheet 26.

The wing-panel 42, and particularly the distal, laterally-outboard wing-sections 43, can be provided with any operative shape. The outline shape can include linear sections, rectilinear sections, polygonal sections, nonlinear sections, curvilinear sections or the like, as well as combinations thereof. Curved sections can be concave or convex, and may have constant or non-constant radii of curvature.

In the various configurations of the invention, the wing panel 42 can be a separately provided component and can be connected to a major facing-surface of the article. In a particular arrangement, the wing panel 42 can be connected to a major facing-surface of the backsheet 28. In particular arrangements, the backsheet 28 can have a backsheet intermediate section interposed between a pair of longitudinally opposed, backsheet end sections, and the wing-panel 42 can be operatively connected in a configuration which can be arranged to operatively extend laterally from the intermediate section of the backsheet 28. The wing-panel may be directly or indirectly joined to the backsheet, as desired.

With reference to FIGS. 1 through 2A, at least an operative portion of an individual, singular wing-panel 42 can extend substantially continuously along an entire cross-directional width of a corresponding region of the topsheet 26 and/or backsheet 28. In particular features, the wing-panel can have a contiguous substantially unitary structure, and at least a significant portion of a medial section of the wing-panel 42 can be arranged to extend along and across an entire cross-directional width of the corresponding region(s) of either or both of the topsheet and backsheet. At least a significant portion of the medial section of the wing-panel 42 can also be arranged to extend along and across an entire cross-directional width of the corresponding region of the absorbent body 30. Additionally, a pair of distal laterally-opposed side portions 43 of the wing-panel 42 can extend from lateral sides of the wing-panel medial section, and can extend laterally beyond the pair of laterally-opposed, terminal side edges of the backsheet and/or topsheet. Examples of an absorbent article having a singular wing-panel are described in detail in U.S. patent application Ser. No. 10/785,143 entitled FEMININE SANITARY NAPKIN OR OTHER ABSORBENT ARTICLE HAVING PLACE AND CUT WINGS by G. Alcantara et al., which was filed Feb. 24, 2004, the entire disclosure of which is incorporated herein by reference in a manner that is consistent herewith.

In desired arrangements, the laterally-opposed side portions (e.g. wing-sections 43) of the wing-panel 42 can extend laterally beyond the pair of laterally-opposed, terminal side edges 62 of the backsheet 28. The wing-panel may be joined or otherwise connected to a bodyside surface of the backsheet, or may be connected to an outward, garment-side surface of the backsheet. Additionally, at least a significant portion of the wing-panel 42 can be arranged to extend along and across an outward, garment-side surface of the absorbent body 30. The wing-panel may also be configured to provide an immediately adjacent contact with at least a portion of the garment-side surface of the absorbent body.

The wing-panel material should be strong enough to process well and not tear or rip while the final article is in ordinary use. The wing-panel material can, for example, have a thickness within the range of about 0.25 mm–3.0 mm, and may exhibit a desired porosity value.

Where the wing-panel is connected to an inward, bodyside surface or an outward, garment-side surface of the backsheet, the wing-panel may be liquid-permeable or may be operatively liquid-impermeable, as desired. Particular configurations can include a breathable nonwoven fabric, a non-breathable nonwoven fabric, a spunbond fabric, a carded web, a thermally bonded web, a breathable film material, a non-breathable film or the like, as well as combinations thereof. Suitable breathable materials can typically have a Water Vapor Transmission Rate (WVTR) of at least a minimum of 700 grams of water per square meter of material per 24 hr ($g/m^2 24$ hr) and can have a WVTR of at least about 1200 g/m2/24 hr. WVTR testing is a conventional test that is well known to those skilled in the art of breathable materials. For example, see INDA IST. 70.4–99 "Standard Test Method for Water Vapor Transmission Rate Through Nonwoven and Plastic Film using a Guard Film and Vapor Pressure Sensor", developed by the Association of the Nonwoven Fabrics Industry (formerly the International Nonwovens and Disposables Association). Suitable testing systems are available from commercial vendors, such as Mocon, Inc., a business having offices located in Minneapolis, Minn., U.S.A.

In desired configurations, at least an operative portion of the wing-panel 42 can alternatively extend substantially continuously along an entire cross-directional width of a corresponding region of the topsheet 26. Additionally, laterally-opposed side portions of the wing-panel 42 can extend laterally beyond the pair of laterally-opposed, terminal side edges of the topsheet 26. The wing-panel 42 can optionally be connected to a major facing-surface of the topsheet 26. More particularly, the wing panel may be operatively connected to a bodyside surface of the topsheet or to an outward, garment-side surface of the topsheet. The wing-panel 42 can also be arranged to extend along and across an inward, bodyside surface of the absorbent body 30. Additionally, the wing-panel may be configured to provide an immediately adjacent contact with at least a portion of the bodyside surface of the absorbent body.

In still other aspects, the wing-panel 42 may be configured to extend between selected component layers or strata of the absorbent body 30, and in particular arrangements, can be sandwiched between the selected absorbent body components. For example, the wing-panel 42 can be located and interposed between an intake layer 32 and a retention layer 36 of the absorbent body 30. Where the wing-panel 42 is provided by a singular component, an operative medial portion of the wing-panel 42 can extend substantially continuously along the entire cross-directional width of a corresponding region of the absorbent body. In particular, the wing-panel can extend substantially continuously along the entire cross-directional widths of corresponding regions of the intake layer and retention layer.

Where the wing-panel is positioned to extend adjacent the topsheet or between selected components of the absorbent body 30, the wing-panel can be composed of a liquid-permeable material. Additionally, the material may be configured to provide improved intake, distribution and/or retention of liquid, thereby providing additional absorbency benefits.

Figure 4:
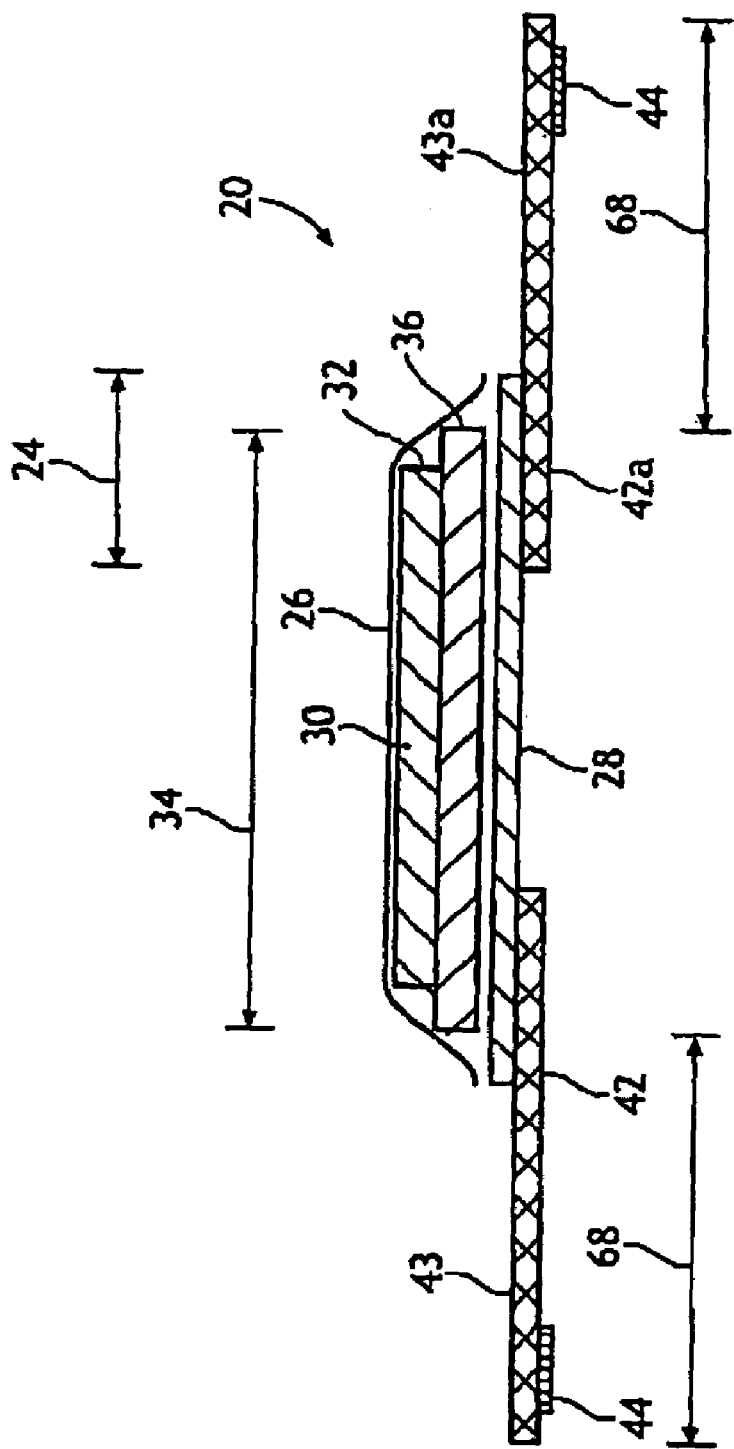
FIG. 4 shows a partially-expanded schematic view of a representative laterally extending, transverse cross-section through an article having a plurality of wing-panels positioned against a garment-side surface of a backsheet of the article.

With reference to FIGS. 3 through 4, the article 20 can alternatively include at least one cooperating pair of wing-panel members 42, 42a. Desirably, each pair of wing-panel members can be operatively, laterally aligned with each other along the transverse cross-direction 24. The pair of wing-panel members 42, 42a can be substantially mirror-images of each other. Additionally, the terminal, inboard edges of each cooperating pair of wing-panel members can be laterally spaced-apart by a discrete lateral distance. With respect to each cooperating pair of wing-panels, a first, separately provided wing-panel component or member has a construction and configuration that can be arranged to extend laterally outward from a first laterally-terminal side edge of the topsheet 26 and/or backsheet 28. A second, separately provided wing-panel component or member 42a can extend laterally outward from a second laterally-terminal side edge of the topsheet 26 and/or backsheet 28.

Each of the individual wing-panel members 42, 42a can be operatively connected and attached to the article 20 in accordance with the various configurations pertaining to the singular wing-panel that are disclosed herein. For example, either or both of the wing-panel members 42, 42a can be joined or otherwise connected to a garment-side or bodyside surface of the backsheet 28, and/or a garment-side or bodyside surface of the topsheet 26, as desired. In the various configurations of the article, any or all of the wing-panels can be operatively attached to the article 20 with hotmelt adhesive. It should be readily appreciated, however, that any other operative adhesive or attachment mechanism may alternatively be employed. Such mechanisms can include thermal bonds, ultrasonic bonds, stitches, pins, staples, rivets or the like, as well as combinations thereof.

In a particular feature of the invention, each wing-panel (42, 42a) can include an operative quantity of an operative odor-control material. The odor-control material can operatively enhance a desired discreet disposal of soiled absorbent articles. Additionally, the distinctive configuration of each employed wing-panel can help trap malodorous volatiles.

Any operative odor-control material can be employed with the selected wing-panel. The odor-control material can, for example, include a fragrance, an odor-masking agent, an odor-neutralizing agent, an odor absorbent, an odor adsorbent or the like, as well as combinations thereof. A broad range of odor adsorbents may be desired for their ability to effectively adsorb a variety of odor constituents. Such adsorbents can include, for example, zeolites and activated carbon. Other suitable odor-control materials are well-known in the art and commercially available. The odor-control materials can be operatively incorporated into each wing-panel by employing well known, conventional techniques. For example, the odor-control materials can be incorporated by impregnating a base sheet with the odor-control material, or by laminating the odor-control between selected base sheet materials. Alternative techniques for incorporating the odor-control material into the wing-panel can include coating, spraying, printing, or the like, as well as combinations thereof. Coating the materials onto a base sheet may be a preferred processing method due to the ability to provide a controlled application of the odor-control materials and the ability to provide a strong, post-process attachment. In a particular configuration, the odor-control material may include an activated carbon-coated film produced by utilizing a commercially available MEAD/WESTVACO carbon ink technology. In a particular formulation, for example, the carbon ink can include 14–16 wt % activated carbon, 11–14 wt % styrene-acrylic copolymer, and 70–75 wt % water This technology is available from Meadwestvaco Corp., a business having offices located in Covington, Va., U.S.A. A porous base sheet, such as tissue or fabric, can be coated by employing a dip and squeeze saturation method, while a nonporous base sheet, such as film, can be coated by employing a direct printing. For example, a film material can be pretreated with corona discharge and coated by employing a commercially available, direct gravure printing process. The applied coating can be dried by employing a through-air drier with set points of about 180–190° F. The add-on weights of the coating can be within the range of about 0.6–10 g/m$^2$, and the desired coating can be produced at speeds up to about 1000 ft/min (about 305 m/min). The coating of the activated carbon may be applied across the full surface of the base sheet material or in a patterned design to communicate the presence of odor-control benefits, enhance aesthetics, or to communicate a feeling of well-being or other desired information.

The wing-panel 42 may be configured to release, trigger or activize the employed odor control material upon an initial stretching, pulling or other manipulation of the wing-panel material. In a desired feature, however, the odor control material can be arranged to be in an operative, activized configuration substantially without conducting an initializing manipulation of the wing-panel.

In a particular feature of the invention, the distal wing-sections 43 of the wing-panel or wing-panels can be employed to hold the article 20 in a desired disposal condition, and provide an outermost layer that produces an operative level of odor-control. The distal wing-sections 43 can at least partially wrap about or partially enclose the absorbent body 30, and in desired arrangements may substantially completely wrap about or enclose the absorbent body. Where the article includes a singular wing panel, for example, the wing-panel can be arranged to extend completely around the article when the article is in the desired disposal condition. Where the article includes a cooperating pair of laterally opposed wing-panels, the wing-panels may extend only partially around the article when the article is in the desired disposal condition.

Figure 5:
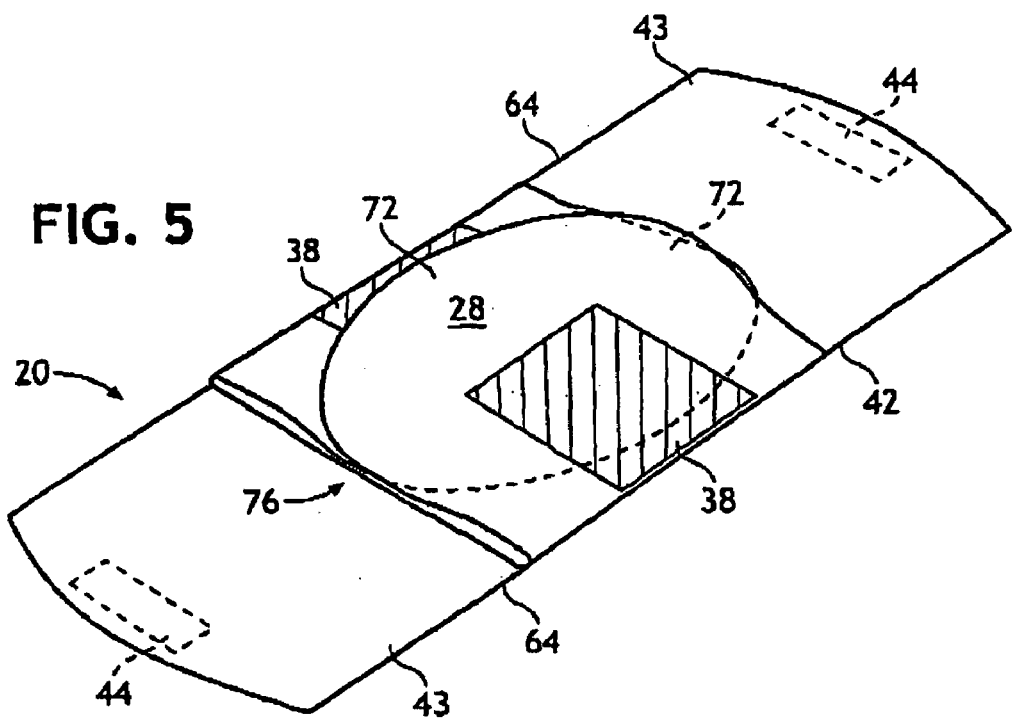
FIG. 5 shows a schematic, perspective view of a representative article having a singular wing-panel in which end portions of the article are folded onto the intermediate portion of the article.
Figure 5A:
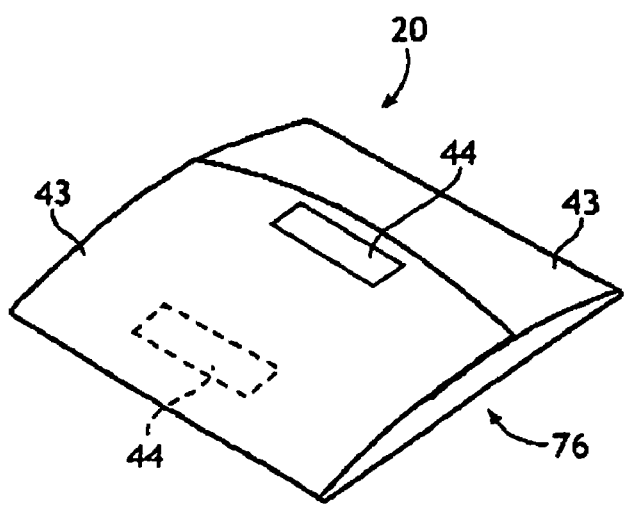
FIG. 5A shows a schematic, perspective view of the representative article of FIG. 5 in which the distal sections of the wing-panel are folded onto the previously folded end portions of the article to provide a disposal condition.

With reference to FIGS. 5–5A, for example, the article 20 can have a singular wing-panel 42, and the end portions 72 of the article can be folded, rolled or otherwise repositioned onto the article intermediate portion 76 to initiate the formation of the disposal condition. After the repositioning of the article end portions 72, the distal wing-sections 43 of the wing-panel can be disposed over the absorbent body to complete the formation of the desired disposal condition. Additionally, the panel-fasteners 44 can be configured to help hold the wing-panels over the folded end portions, and help secure and maintain the article in the disposal condition.

Figure 6:
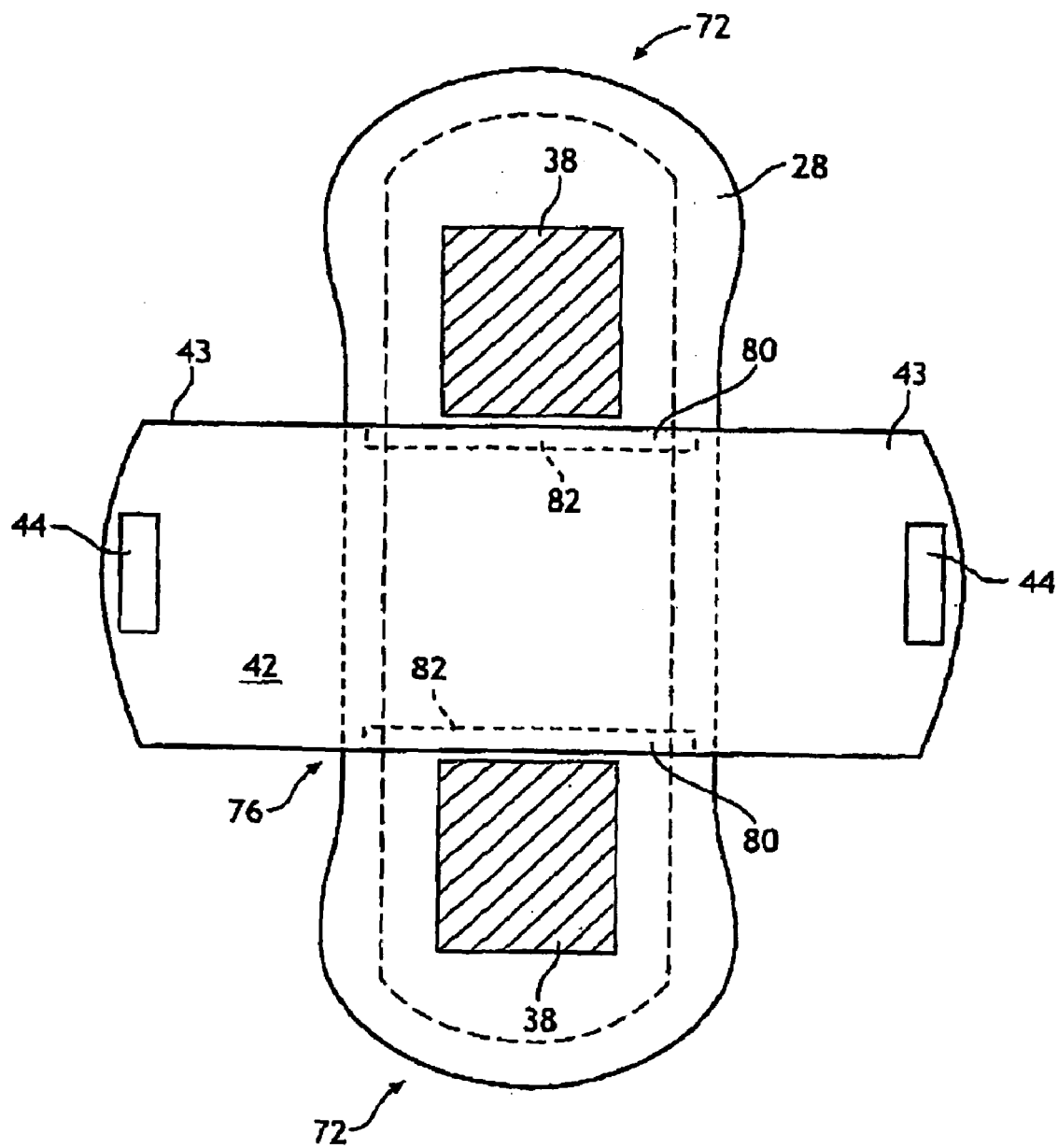
FIG. 6 shows a top, plan view of a garment-side of a representative article having a singular wing-panel positioned adjacent the outward, garment-side surface of the article backsheet, in which edge regions of the wing-panel are releasably attached to the backsheet.
Figure 7:
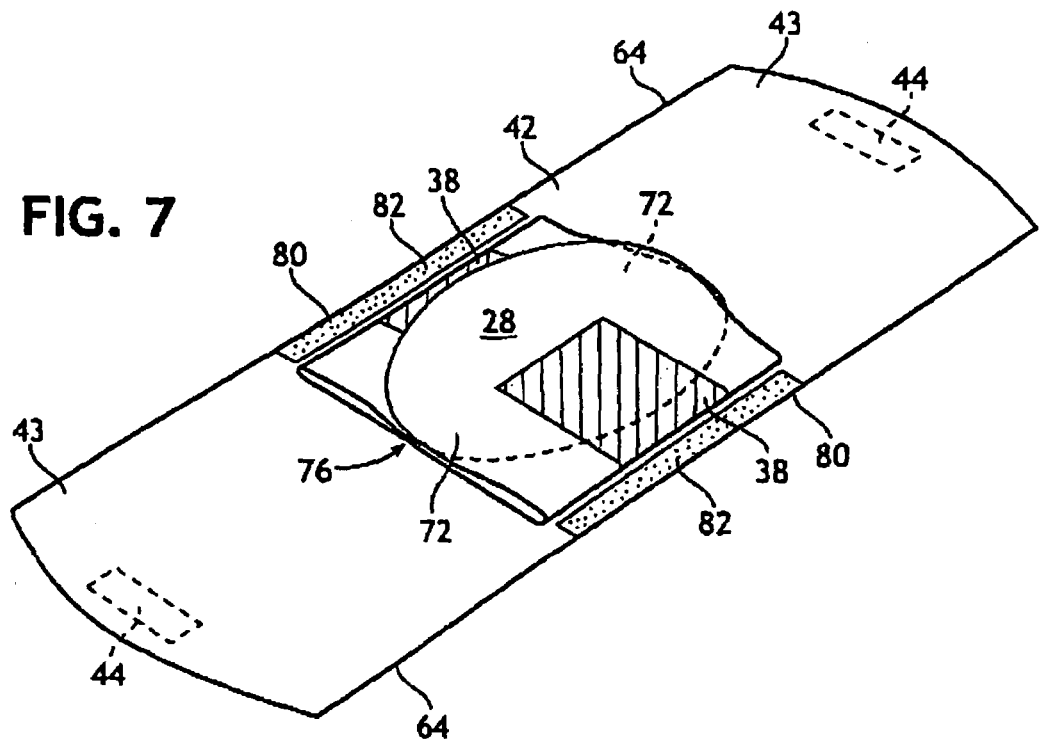
FIG. 7 shows a schematic, perspective view of the article of FIG. 6 in which end portions the article are folded onto the intermediate portion of the article.
Figure 7A:
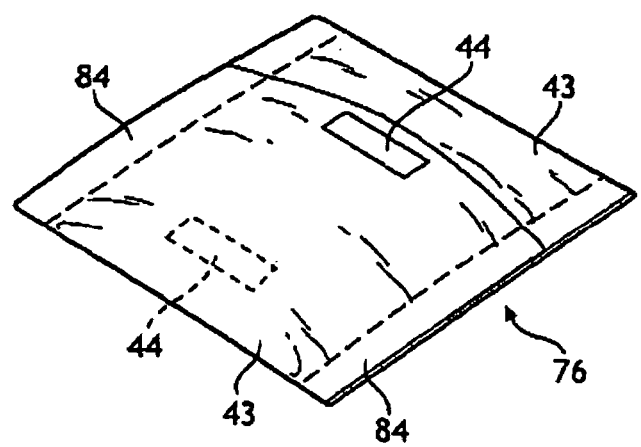
FIG. 7A shows a schematic, perspective view of the article of FIG. 7 in which the distal sections of the wing-panel are folded onto the previously folded end portions of the article, and the edge regions of the wing-panel are operably attached to provide a further securement of the article in the disposal condition.

With reference to FIGS. 6–7A, for example, a further aspect of the invention can include a singular wing-panel 42 or a set of wing-panels (42, 42a) wherein the wing-panel has at least one laterally extending, edge-region 80 that can be releasably connected to the backsheet 28. As representatively shown, the selected edge-region 80 can be positioned on a laterally-extending, intermediate section of the wing-panel, which is positioned between the laterally opposed, distal wing-sections 43. Alternatively or additionally, the selected edge-region can be located on other portions of the wing-panel. Desirable configurations can include an employed wing-panel that has at least a pair of longitudinally-opposed edge-regions that are releasably connected to the backsheet. The wing-panel can be operatively disposed on the garment-side of the backsheet, and each edge-region can include an operative edge-fastener 82 that is located in its corresponding edge-region. Each edge-fastener can have any operative location and construction. As representatively shown, for example, each edge-fastener can be located on a bodyside of the wing-panel, and can be operatively configured to releasably attach to the backsheet 28.

As representatively shown in FIGS. 6 and 7, for example, the article 20 may have a singular wing-panel 42, and the end portions 72 of the article can be folded, rolled or otherwise repositioned onto the article intermediate portion 76 to initiate the formation of the disposal condition. During the repositioning of the article end portions, the edge-regions 80 can be detached or otherwise separated from the backsheet 28. Thereafter, the distal wing-sections 43 of the wing-panel can then be disposed over the previously folded end portions to continue the formation of the desired disposal condition. Additionally, the panel-fasteners 44 can be configured to help hold the wing-panels over the folded end portions, and help secure and maintain the article in the disposal condition. In a further feature, the folded-over portions of the edge regions 80 of the distal wing-panel sections 43 can be attached to the edge-fastener 82 to form at least one operative edge-attachment 84. Desirably, an operative edge-attachment can be formed along each of the laterally-extending, longitudinally-opposed edges of the folded article. Each edge-attachment 84 can provide an edge seal which can help hold the folded article in the disposal condition, and help contain malodors within the folded article.

The edge-fastener 82 can include any operative fastening mechanism. For example, the edge-fastener can include a component of an interengaging mechanical fastener, an adhesive fastener, a cohesive fastener, a magnetic fastener, and electromechanical fastener or the like, as well as combinations thereof.

Each wing-panel 42, or any desired combination of the employed wing-panels, can include a panel-fastener component 44 which is operatively connected to an appointed engagement surface of the associated wing-panel. The panel-fastener 44 can include any operative fastener component, such as a component of an interengaging mechanical faster, an adhesive fastener, a cohesive fastener, a magnetic fastener, an electromechanical fastener or the like, as well as combinations thereof.

For example, each panel-fastener 44 can include a hook or other "male" component of an interengaging mechanical fastener system. Any operative hook component may be employed. For example, a suitable hook component material can include a J-hook, mushroom-head hook, flat-top nail-head hook, a palm-tree hook, a multiple-J hook or the like, as well as combinations thereof.

An operative first section of the selected hook component can be connected to a major facing surface of at least a first wing-panel portion 42, and can be configured to contact or otherwise engage a cooperating, second wing-panel portion during ordinary use. Additionally, an operative second section of a hook component, composed of the same or different type of hook material, can be connected to a major facing surface of the second wing-panel portion, and can be configured to contact or otherwise engage an outward surface of the wearer's undergarment during ordinary use. For example, the hook component can be arranged to operatively engage and removably attach to the outward surface of a crotch region of the undergarment.

Each wing-panel 42, or any desired combination of the employed wing-panels, can include a cooperating, second fastener-component. For example, the second fastener-component can be a loop or other "female" component of an interengaging mechanical fastener system. Any operative loop component may be employed. For example, a suitable loop component material can include a woven fabric, a knit fabric, a nonwoven fabric, a fabric laminated to a substrate or the like, as well as combinations thereof.

An operative first section of a selected loop component can be joined or otherwise operatively connected to a major facing surface of at least the second wing-panel portion, and can be configured to contact or otherwise engage the hook component on the first wing-panel portion 42 during ordinary use. Additionally, an operative second section of a loop component, composed of the same or different type of loop material, can be connected to a major facing surface of the first wing-panel portion 42. As a result, the user can have the option of alternatively attaching the second hook component of the second wing-panel onto the second loop component of the first wing-panel. Accordingly, the first hook component may alternatively be engaged with the outward surface of the wearer's undergarment.

Each or any desired combination of the provided loop components may be a separately provided member that is subsequently connected and assembled to its corresponding wing-panel portion 42. In a desired feature, each or any desired combination of the provided loop components can be integrally provided by the material employed to construct its corresponding wing-panel portion.

In the various arrangements of the present invention, the hook component can be configured to have a particularly selected hook concentration or density (hooks per unit area). In a particular aspect, the hook density can be within the range of about 1500–7000 hooks/in$^2$ (about 232–1085 hooks/cm$^2$). The hook density can alternatively be within the range of about 2000–6000 hooks/in$^2$ (about 310–930 hooks/cm$^2$), and can optionally be within the range of about 3000–5000 hooks/in$^2$ (about 465–775 hooks/cm$^2$) to provide improved performance. Examples of suitable hook materials can include 85-Series and 61-Series hook materials available from Velcro, U.S.A., a business having offices located in Manchester, N.H., U.S.A. The hook materials can, for example, have a hook density of about 775 hooks/cm$^2$.

In a particular aspect, the material of the loop component may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. patent application Ser. No. 754,419 entitled PATTERN-UNBONDED NONWOVEN WEB AND PROCESS FOR MAKING THE SAME, by T. J. Stokes et al., and filed Dec. 17, 1996; the entire disclosure of which is incorporated herein by reference in a manner that is consistent herewith.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A personal care absorbent article having a longitudinal-direction, a lateral cross-direction, and an intermediate portion interposed between a pair of longitudinally opposed end portions, said article comprising
    a backsheet having a pair of laterally-opposed side edges, a laterally-extending backsheet width, and a longitudinally-extending backsheet length;
    a liquid-permeable topsheet;
    an absorbent body sandwiched between said backsheet and said topsheet; and
    a separately provided wing-panel which is operatively connected to the intermediate portion of said article, and extends laterally beyond at least one lateral side edge of said backsheet in the intermediate portion of said article, said wing-panel configured to wrap about an undergarment;
wherein
    said wing-panel includes an operative quantity of odor-control material;
    a maximum longitudinal length of said wing-panel is less than said overall article-length;
    said wing-panel can be configured to operatively provide a wing-section distance which is at least about 50% of a width of the absorbent body;
    the wing-panel is connected to a major garment-side surface of said backsheet;
    the wing-panel has at least one laterally-extending edge-region;
    the at least one laterally-extending edge-region of the wing-panel is configured to be separated from the backsheet when the end portions of the article are repositioned onto the article intermediate portion to initiate a formation of a disposal condition;

the wing-panel includes a distal wing-section which can be disposed over the previously folded end portions to continue the formation of the disposal condition;

a folded-over portion of the edge-region in the distal wing-panel section is configured to be attached with an edge-fastener to form at least one operative edge-attachment; and the at least one edge-attachment is configured to provide an edge seal which can help hold the folded article in the disposal condition.

2. An article as recited in claim 1, wherein said wing-panel has at least a longitudinally-opposed pair of the laterally-extending edge-regions;

each of the pair of laterally-extending edge-regions of the wing-panel is configured to be separated from the backsheet when the end portions of the article are repositioned onto the article intermediate portion to initiate a formation of a disposal condition;

the wing-panel includes a laterally-opposed pair of distal wing-sections each of which can be disposed over the previously folded end portions to continue the formation of the disposal condition;

a folded-over portion of each of the pair laterally-extending edge-regions in each of said pair of distal wing-panel sections is configured to be attached with a corresponding edge-fastener to form an operative, corresponding edge-attachment; and each corresponding edge-attachment is configured to provide an edge seal which can help hold the folded article in the disposal condition.

3. An article as recited in claim 2, wherein each corresponding edge-attachment is also configured to help contain malodors within the disposal condition of the folded article.

4. An article as recited in claim 2, wherein at least an operative portion of said wing-panel extends substantially continuously along an entire cross-directional width of a corresponding region of said backsheet;

said wing-panel extends laterally beyond the pair of laterally-opposed, terminal side edges of said backsheet; and each of the pair of laterally-extending edge-regions of the wing-panel is positioned on a laterally-extending, intermediate section of the wing-panel that is positioned between the laterally opposed, distal wing-sections.

5. An article as recited in claim 1, further including a garment-fastener connected to a garment-side surface of the backsheet; wherein said wing-panel is connected onto a garment-side surface of said backsheet, and said wing-panel has a garment-side surface;

at least an operative portion of said wing-panel extends substantially continuously along an entire cross-directional width of a corresponding region of said backsheet;

said wing-panel extends laterally beyond the pair of laterally-opposed, terminal side edges of said backsheet; and said garment-side surface of the wing-panel is substantially free of said garment-fastener.

6. An article as recited in claim 1, wherein said wing-panel has at least one laterally extending, edge region that is releasably connected to said backsheet by the edge-fastener.

7. An article as recited in claim 1, further including a garment-fastener connected to a garment-side surface of the backsheet; wherein the garment-fastener has a garment-fastener width which is at least about 30% of a width of the absorbent body.

8. An article as recited in claim 1, further including a garment-fastener connected to a garment-side surface of the backsheet; wherein the garment-fastener has a garment-fastener width which is at least about 60% of a width of the absorbent body.

9. An article as recited in claim 1, further including a garment-fastener connected to a garment-side surface of the backsheet; wherein the garment-fastener is distributed in a pattern in which the garment-side surface of the wing-panel is substantially free of said garment-fastener.

10. An article as recited in claim 1, further including a garment-fastener connected to a garment-side surface of the backsheet; wherein the garment-fastener is configured to be substantially absent from the intermediate portion of the article along a longitudinally extending, zone distance length.

11. An article as recited in claim 1, further including a garment-fastener connected to a garment-side surface of the backsheet; wherein the garment-fastener is configured to be substantially absent from the intermediate portion of the article along a longitudinally extending, zone distance length which is at least about 15% of a backsheet length.

12. An article as recited in claim 1, further including a garment-fastener connected to a garment-side surface of the backsheet; wherein the garment-fastener is configured to be substantially absent from the intermediate portion of the article along a longitudinally extending, zone distance length which is at least about one-third of a backsheet length.

13. An article as recited in claim 1, wherein the wing-section distance is at least 60% of a width of the absorbent body.

14. An article as recited in claim 1, wherein the wing-section distance is at least 60% of an absorbent body width, and up to about 75% of the absorbent body width.

15. An article as recited in claim 1, wherein said wing-section distance is at least about 3 cm.

16. An article as recited in claim 1, wherein said wing-panel is extensible and can be operatively configured to provide said wing-section distance by extensibly enlarging the wing-panel.

17. An article as recited in claim 1, wherein the odor-control material includes an activated carbon.

18. An article as recited in claim 1, wherein the odor control material is arranged to be in an operatively activated configuration substantially without conducting an initializing manipulation of the wing-panel.

* * * * *